(12) United States Patent
Buck (10) Patent No.: US 11,951,334 B2
(45) Date of Patent: Apr. 9, 2024

(54) PATIENT POSITIONING DEVICE

(71) Applicant: BEC GmbH, Pfullingen (DE)

(72) Inventor: Matthias Buck, Reutlingen (DE)

(73) Assignee: BEC GmbH, Pfullingen (DE)

( * ) Notice: Subject to any disclaimer, the term of this patent is extended or adjusted under 35 U.S.C. 154(b) by 560 days.

(21) Appl. No.: 17/231,069

(22) Filed: Apr. 15, 2021

(65) Prior Publication Data
US 2021/0353486 A1   Nov. 18, 2021

(30) Foreign Application Priority Data

May 12, 2020   (EP) ..................................... 20174076

(51) Int. Cl.
*A61N 5/10* (2006.01)
(52) U.S. Cl.
CPC ............. *A61N 5/1083* (2013.01); *A61N 5/10* (2013.01); *A61N 2005/109* (2013.01); *A61N 2005/1094* (2013.01)
(58) Field of Classification Search
CPC ...... A61N 5/1083; A61N 5/10; A61N 5/1049; A61N 5/1069; A61N 2005/109; A61N 2005/1094; A61N 2005/1097; A61B 6/0464; A61B 6/0487; A61B 6/107; A61B 34/30; A61B 34/70; B25J 18/00; G21F 7/06; A61G 13/00
USPC ..................................................... 250/515.1
See application file for complete search history.

(56) References Cited

U.S. PATENT DOCUMENTS 10,492,736 B2   12/2019   Papalazarou et al.
2020/0405403 A1*  12/2020   Shelton, IV ....... A61B 17/3421

FOREIGN PATENT DOCUMENTS

DE   10 2006 020 868   10/2007
EP       1 985 237       10/2008

OTHER PUBLICATIONS

Allgower C.E., et al.; "Experiences with an application of industrial robotics for accurate patient positioning in proton radiotherapy"; Int J Med Robotics Comput Assist Surg 2007; 3: 72-81; published online in Wiley InterScience.

* cited by examiner

*Primary Examiner* — Kiet T Nguyen
(74) *Attorney, Agent, or Firm* — Gudrun E. Huckett (57) ABSTRACT

A patient positioning device has a robot arm and a patient receptacle held at the robot arm. The patient positioning device has a housing assembly for the robot arm. The housing assembly is provided with one or more housing units surrounding the robot arm at least partially. The one or more housing units are secured at the robot arm. The patient positioning device is provided with a shielding against ionizing radiation. At least one part of the shielding is arranged at the one or more housing units.

18 Claims, 6 Drawing Sheets

PATIENT POSITIONING DEVICE

BACKGROUND OF THE INVENTION

The invention relates to a patient positioning device, in particular for the boron neutron capture therapy (BNCT), comprising a robot arm and a patient receptacle held at the robot arm.

EP 1 985 237 A1 discloses a patient positioning device which comprises a robot arm and a patient receptacle held at the robot arm.

When irradiating tumor tissue, ionizing radiation is used. In particular the radiation employed in boron neutron capture therapy (BNCT) is very aggressive and damages in particular electronic components. For protecting electronic components from ionizing radiation, shielding devices are known that are commercially available in the form of plates or foil, for example.

The invention has the object to provide a patient positioning device of the aforementioned kind that can be used in an environment with ionizing radiation and that is of a simple configuration.

SUMMARY OF THE INVENTION

This object is solved by a patient positioning device characterized in that the patient positioning device comprises a housing assembly for the robot arm that comprises at least one housing unit that surrounds the robot arm at least partially, wherein the housing unit is secured at the robot arm, and characterized in that the patient positioning device comprises a shielding against ionizing radiation, wherein at least one part of the shielding is arranged at the housing unit.

Robot arms that are used in connection with patient positioning devices are often no custom-made products for patient positioning but conventional robot arms used in industrial manufacturing. Such robot arms have no shielding against ionizing radiation. In order to be able to use such a robot arm for the patient positioning device, the present invention provides a housing assembly for the robot arm that comprises at least one housing unit which surrounds the robot arm at least partially. The housing unit is secured at the robot arm. Thus, the housing unit moves together with the robot arm in operation. The patient positioning device comprises a shielding against ionizing radiation wherein at least a part of the shielding is arranged at the housing unit. According to the invention, it is therefore provided that the shielding is not arranged immediately at the robot arm itself but at a housing unit which at least partially surrounds the robot arm.

Since the shielding is not provided at the robot arm but at the housing unit surrounding the robot arm, the shielding can be arranged at least partially at a distance from the robot arm. This is advantageous in particular in the region of drives which heat up during operation. Due to the distance, damage to the shielding by the heat is prevented, on the one hand, and a satisfactory air circulation about parts of the robot arm that heat up, for example, about the drives, can be ensured, on the other hand.

Since the shielding is not arranged immediately at the robot arm, a configuration of the shielding with a geometry that is deviating from that of the robot arm is possible. The geometry of the housing unit can be adapted to the geometric requirements of the shielding. The at least one housing unit can be designed such that the shielding can be attached in a simple way to the housing unit, for example, in the form of a foil or a plate or a plurality of plates. The housing unit comprises for this purpose advantageously a smooth geometry with soft transitions and no edges or only a few edges. A geometry with a large surface area is particularly advantageous for applying a shielding. Advantageous are, for example, geometries which are based on a cuboid with rounded corners, a truncated cone, a truncated pyramid with rounded corners, a sphere, an ellipsoid, a semi-sphere, a cylinder or other geometric basic shapes.

Advantageously, the housing unit comprises at least one removable cover. Advantageously, at least a part of the shielding is held at the cover and can be removed together with the cover. In this way, the housing unit can be designed such that components of the robot arm that are to be serviced or repaired are easily accessible by removing the cover. Since the shielding is held at the cover and removable together with it, damage to the shielding, for example, during service work at the robot arm, is reliably prevented. In this way, a long service life of the usually very expensive shielding is enabled. Since the shielding is not arranged immediately at the robot arm, for example, glued onto it, but instead is removable at least partially with a cover of the housing unit, it is prevented that the shielding can be damaged during service or repair work and must thus be partially or completely exchanged.

In an advantageous configuration, all parts of the shielding for the robot arm are fixed at the housing assembly. Preferably, all sections of the housing assembly are provided with the shielding, in particular completely lined with the shielding.

In an advantageous configuration, the shielding is arranged at the inner side of the housing unit. In this way, the shielding is protected from external mechanical effects and possible damages associated therewith.

Advantageously, the robot arm comprises a plurality of sections which are movable relative to each other. In an advantageous configuration, a separate housing unit is provided for each section of the robot arm. In this way, the housing units can move together with the respective sections of the robot arm and, in a simple way, it is prevented that, when the robot arm is moving, regions of the robot arm exit from the housing assembly and can thus be exposed to ionizing radiation.

A simple configuration results when at least one housing unit comprises a base body fixed at the section of the robot arm and a cover detachably held at the base body. A plurality of base bodies and/or a plurality of covers can be provided also in this context. It can also be provided that the base body and/or the cover is constructed of a plurality of components that are fixedly connected to each other. In an advantageous configuration, screw connection points which are provided at the robot arm anyway are used for the fixation of the base body at the robot arm so that a fixation of the at least one base body at the robot arm is possible in a simple way. The base body is advantageously configured such that it must not be removed for usual service and repair work. Therefore, for the attachment of the base body at the robot arm, an attachment that is more complex in regard to detachment is also conceivable. The attachment of the base body at the robot arm can advantageously be arranged partially or completely in the housing interior of the housing unit. The attachment of the base body at the robot arm can comprise, for example, brackets or clamping profiles which extend in the housing interior. The cover is advantageously fixed at the base body by means of fastening means that are easily accessible from the exterior. The position of the fastening means can be selected such that a good accessibility is provided because the position of the fastening means of the cover at the base body is independent of the position of possible screw connection points of the robot arm.

In order to simplify mounting of the cover at the base body, it is advantageously provided that at least one housing unit comprises means for positioning the cover relative to the base body. In an advantageous configuration, the means for positioning the cover relative to the base body are formed by a circumferential rim. Individual positioning pins, insertion ramps or the like can be provided also as means for positioning the cover relative to the base body. A different constructive configuration of the means for positioning the cover relative to the base body can be advantageous also.

Advantageously, at least one housing unit is at least partially provided with a damping layer. Such a damping layer can be provided in particular in order to prevent damage upon collision of the robot arm with other objects. An advantageous configuration results in particular when the damping layer is arranged outside of the shielding, i.e., the shielding is thus positioned closer to the housing interior than the damping layer. In this way, the damping action of the damping layer is not changed or impaired by the shielding.

Advantageously, the damping layer is held at a support structure of the housing unit. The support structure is preferably an inner shell of the housing unit. In a particularly preferred embodiment, the shielding is arranged at the inner side and the damping layer at the outer side of the inner shell. A different configuration of the support structure, for example, in the form of individual ribs or in the form of a grid structure, can be advantageous also. In an advantageous configuration, the damping layer is covered by an outer envelope. In this way, a pleasing exterior of the patient positioning device is achieved. Advantageously, the damping layer comprises an elastic damping material. The damping material can be, for example, foam material or the like. The damping layer can comprise, alternatively or additionally, one or a plurality of gas-filled cushions. The damping action of the at least one gas-filled cushion is obtained by the enclosed gas. The enclosed gas is in particular air. The enclosed gas can be used at the same time as a contact sensor, for example, in that pressure fluctuations of the gas are measured. The outer envelope can form a part of the cushion that encloses the gas. It can however also be provided that the gas is arranged in a cushion that, in turn, is covered by an outer envelope.

Particularly preferred, at least one contact sensor is arranged in the damping layer. The contact sensor generates a corresponding signal when the damping layer is compressed, for example, due to undesirable contact with an object, and can control correspondingly the robot arm, for example, can turn it off. Particularly preferred, a plurality of contact sensors are arranged in the damping layer. The contact sensors have advantageously relative to each other a distance of less than 10 cm at every location of the damping layer. In this way, a possible contact in the surface can be determined in a simple way.

The robot arm is preferably a robot arm with at least five, in particular with at least six, rotation movement axes. The robot arm comprises advantageously a base frame, a carousel rotatably supported at the base frame about a first rotation movement axis, a rocker arm rotatably supported at the carousel about a second rotation movement axis, an arm that is rotatably supported at the rocker arm, and a hand supported at the arm. The hand has preferably three rotation movement axes. A different configuration of the robot arm can however be advantageous also.

BRIEF DESCRIPTION OF THE DRAWINGS

An embodiment of the invention will be explained in the following with the aid of the drawing.

DESCRIPTION OF PREFERRED EMBODIMENTS

Figure 1:
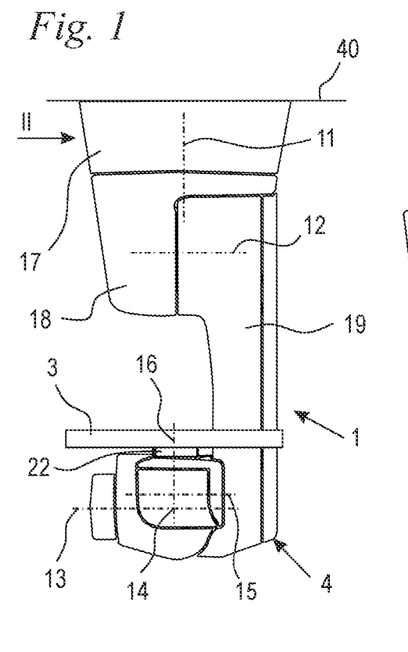
FIG. 1 is a side view of a patient positioning device.
Figure 2:
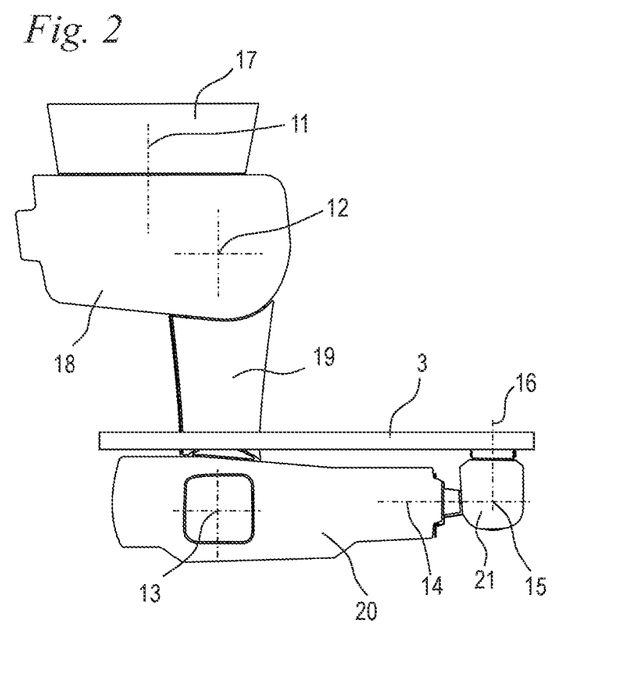
FIG. 2 is a side view of the patient positioning device of FIG. 1 in the direction of arrow II in FIG. 1.

FIGS. 1 and 2 show a patient positioning device 1. Such patient positioning devices 1 are used in order to position patients relative to a radiation device. The beam emitted by the radiation device is in particular a beam of ionizing radiation. Such radiation devices are used in particular in tumor therapy. Particularly preferred, the radiation device is a radiation device for boron neutron capture therapy (BNCT). The patient positioning device 1 comprises a robot arm 2 (FIG. 6) which supports a patient receptacle 3. In the embodiment, the patient receptacle 3 is a patient table. The patient receptacle 3 can also be configured in a different form, for example, as a seat. In the embodiment, the patient positioning device 1 is fixed to the ceiling 40 of the room. A fixation at the floor can be advantageous also.

Figure 3:
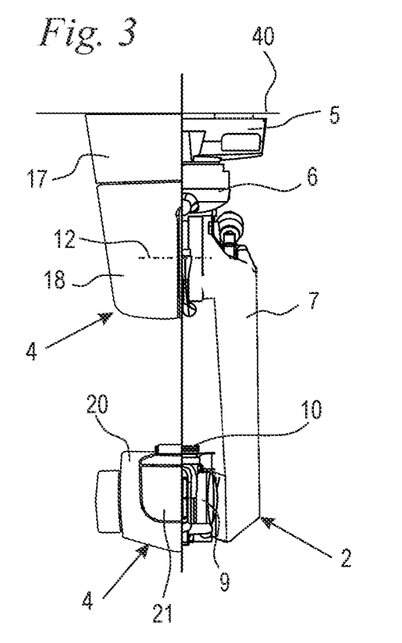
FIG. 3 shows a partially sectioned view of the patient positioning device of FIGS. 1 and 2, wherein the housing assembly is illustrated partially sectioned and, therefore, the robot arm arranged in the housing assembly is visible.
Figure 4:
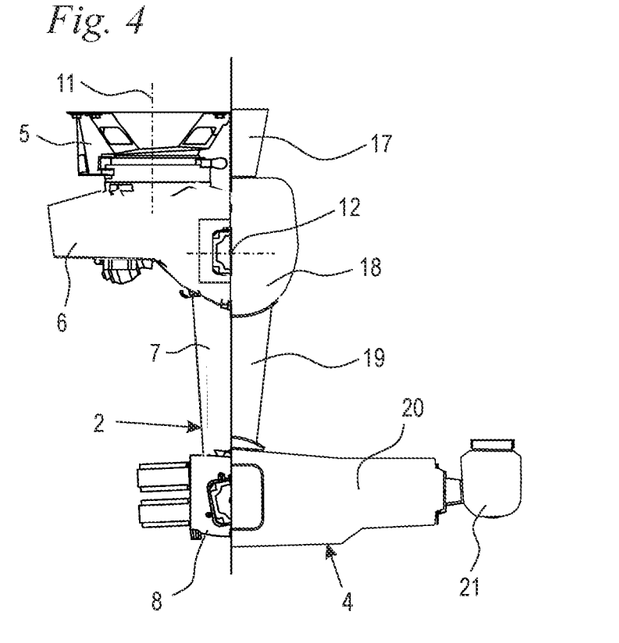
FIG. 4 shows another partially sectioned view of the patient positioning device of FIGS. 1 and 2, wherein the housing assembly is illustrated partially sectioned and, therefore, the robot arm arranged in the housing assembly is visible.
Figure 5:
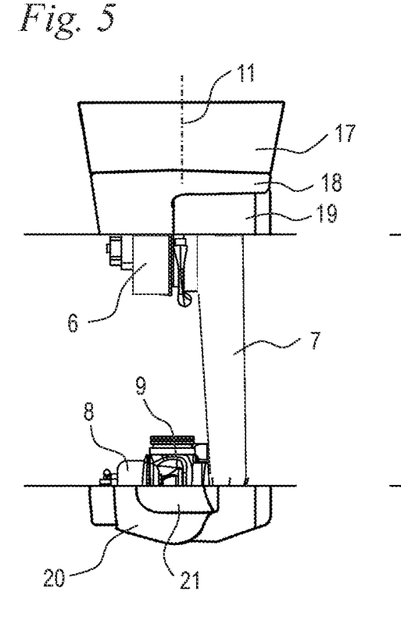
FIG. 5 shows yet another partially sectioned view of the patient positioning device of FIGS. 1 and 2, wherein the housing assembly is illustrated partially sectioned and, therefore, the robot arm arranged in the housing assembly is visible.

As illustrated in FIGS. 3 and 4, the robot arm 2 is surrounded by a housing assembly 4. In FIGS. 1 and 2, the complete housing assembly 4 is illustrated; in FIGS. 3 to 6, it is illustrated partially sectioned so that the robot arm 2 arranged in the housing assembly 4 is visible. The robot arm 2, as shown in FIG. 3, is held immediately at the ceiling 40 of the room. In an alternative embodiment, it can also be provided that the robot arm 2 is fixed at a linear guide which, in turn, is held at the ceiling 40 of the room. The linear guide forms a linear movement device which moves the entire robot arm 2 along a spatial axis, preferably a horizontal spatial axis. In this way, the movement range of the patient positioning device 1 is enlarged. A linear guide which is arranged at the floor can also be advantageous. A different linear movement device can be provided also. When the robot arm 2 is held at a linear movement device, the robot arm 2 can be positioned for radiation treatment such that the robot arm 2 is impacted as little as possible by the ionizing radiation.

The robot arm 2 comprises, as illustrated in FIGS. 3 and 4, a base frame 5. The robot arm 2 comprises in addition a carousel 6, a rocker arm 7, an arm 8, and a hand 9. The hand 9 comprises a fastening flange 10 at which the patient receptacle 3 is fixed.

Figure 6:
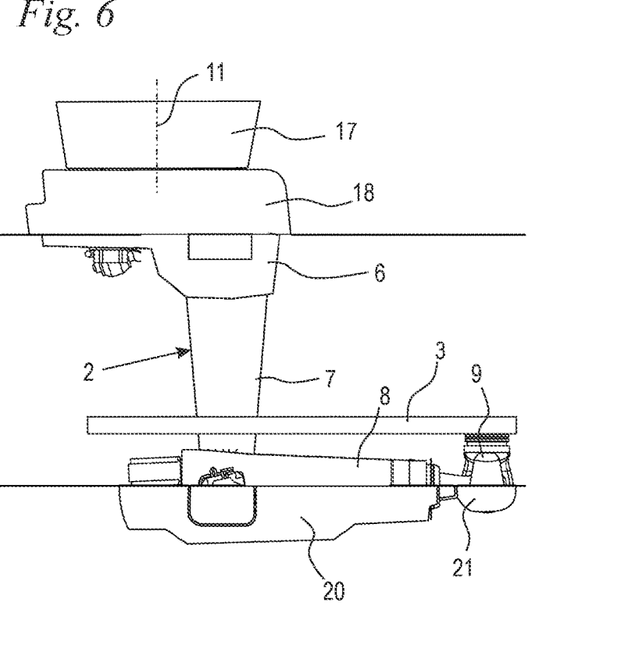
FIG. 6 shows a partially sectioned view of the patient positioning device of FIGS. 1 and 2, wherein the housing assembly is illustrated partially sectioned and, therefore, the robot arm arranged in the housing assembly is visible, and the patient receptacle is illustrated.
Figure 7:
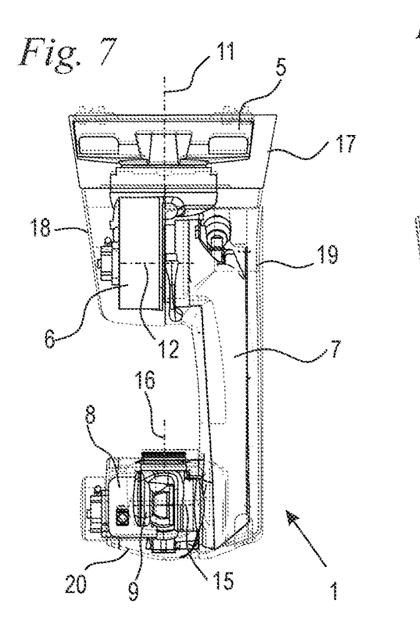
FIG. 7 shows a schematic illustration of the patient positioning device according to the views of FIG. 1 and FIG. 2, wherein the housing assembly is illustrated with dashed line and the robot arm arranged in the housing assembly with solid line, and wherein the patient receptacle and the housing unit at the fastening flange are not illustrated.
Figure 8:
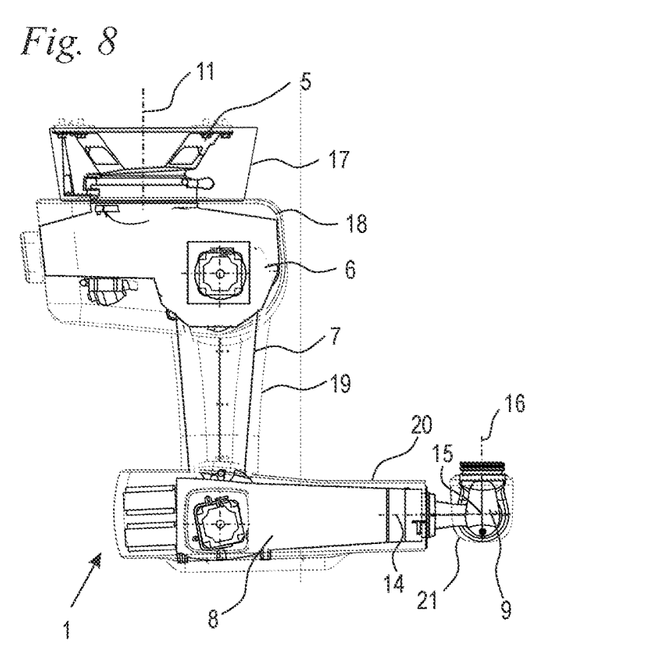
FIG. 8 shows another schematic illustration of the patient positioning device according to the views of FIG. 1 and FIG. 2, wherein the housing assembly is illustrated with dashed line and the robot arm arranged in the housing assembly with solid line, and wherein the patient receptacle and the housing unit at the fastening flange are not illustrated.

The base frame 5 can be fixed at the ceiling 40 of the room or alternatively at a linear guide or at the floor of a room. The carousel 6 is supported at the base frame 5 so as to be rotatable about a first rotation movement axis 11. The first rotation movement axis 11 is vertically oriented in the embodiment. At the carousel 6, a rocker arm 7 is rotatably supported about a second rotation movement axis 12. The second rotation movement axis 12, as shown in FIGS. 1 to 3, is horizontally oriented in the embodiment. The rocker arm 7 is of an elongated configuration. The second rotation movement axis 12 is arranged at one end of the rocker arm 7, and a third rotation movement axis 13 is arranged at the second end of the rocker arm 7. In the embodiment, the third rotation movement axis 13 extends parallel to the second rotation movement axis 12. At the third rotation movement axis 13, which is illustrated in FIGS. 1 and 2, the arm 8 (FIGS. 4 and 6) of the robot arm 2 is pivotably supported. The arm 8 is of an elongated configuration and is rotatably supported in the region of a first end about the third rotation movement axis 13 at the rocker arm 7. In the region of its other end, the arm 8 supports the hand 9. The hand 9, as shown in FIGS. 1, 2, and 3, is rotatably supported at the arm 8 about a fourth rotation movement axis 14. In the embodiment, the fourth rotation movement axis 14 is oriented in the longitudinal direction of the arm 8. The hand 9 comprises a fifth rotation movement axis 15 which is oriented perpendicular to the fourth rotation movement axis 14 and further comprises a sixth rotation movement axis 16 which extends perpendicular to the fifth rotation movement axis 15. The hand 9 comprises the fastening flange 10, visible in FIGS. 5 and 6, at which the patient receptacle 3 is fixed, as shown in FIG. 6.

The base frame 5, the carousel 6, the rocker arm 7, the arm 8 as well as the hand 9 form sections of the robot arm 2 that are movable relative to each other. The housing assembly 4 comprises a plurality of housing units 17 to 22 which surround different sections of the robot arm 2. As shown in FIGS. 1 to 6, a first housing unit 17 is provided which surrounds the base frame 5. A second housing unit 18 surrounds the carousel 6. A third housing unit 19 surrounds the rocker arm 7. A fourth housing unit 20 surrounds the arm 8. A fifth housing unit 21 surrounds the hand 9. A sixth housing unit 22 surrounds the fastening flange 10. There are therefore different housing units 17 to 22 of the housing assembly 4 provided for the sections of the robot arm 2 that are movable relative to each other. The housing units 17 to 22 are configured such that the movement of the robot arm 2 is not impaired by the housing units 17 to 22. At the same time, the housing units 17 to 22 are formed such that the robot arm 2 is mostly, in particular completely, surrounded by the housing assembly 4 in any position of the robot arm 2. The ionizing radiation can advantageously pass only through the housing assembly 4 to the robot arm 2. The housing units 17 to 22 do not enclose the sections of the robot arm 2 completely. The housing units 17 to 22 have openings through which the sections of the robot arm 2 are connected to each other.

Figure 9:
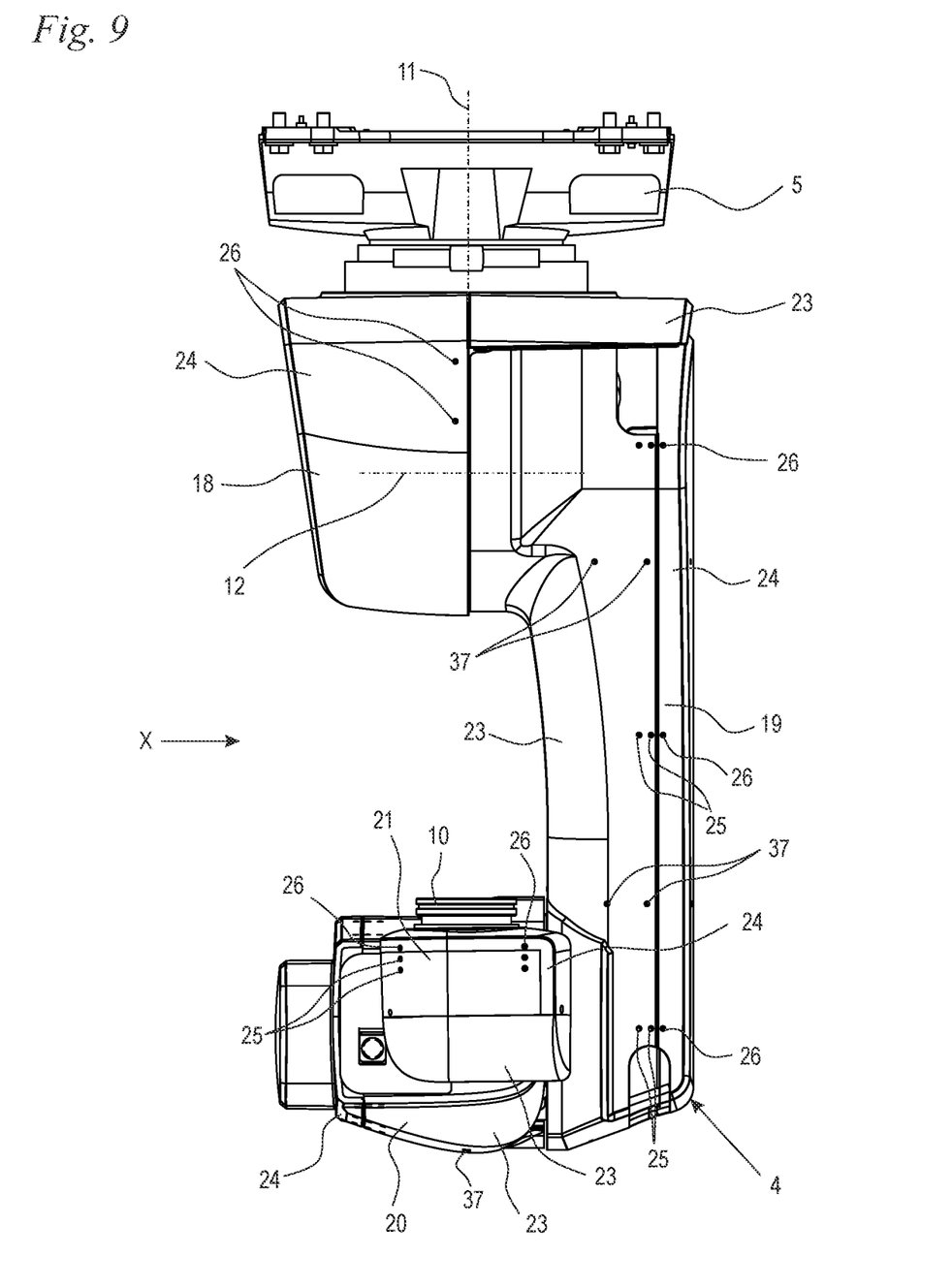
FIG. 9 shows a side view of the patient positioning device corresponding to the view of FIG. 1, wherein the patient receptacle, the housing unit of the base frame, and the housing unit of the fastening flange are not illustrated.

FIG. 9 shows the housing assembly 4 in detail wherein the housing units 17 and 22 are not illustrated.

As shown in FIG. 9, the housing unit 18 comprises a base body 23 as well as a cover 24. The cover 24 is advantageously fixed by fastening screws 26 at the base body 23. Accordingly, the cover 24 can be removed. The base body 23 is advantageously fixed at the robot arm 2 itself. The housing unit 19, surrounding the rocker arm 7, also comprises a base body 23 as well as a cover 24. The base body 23 is fixed, for example, by fastening screws 37 at the robot arm 2. The fastening screws 37 are preferably screwed into already existing screw connection points at the robot arm 2. The fastening screws 26 are arranged adjacent to two fastening screws 25 at the base body 23, respectively.

Figure 11:
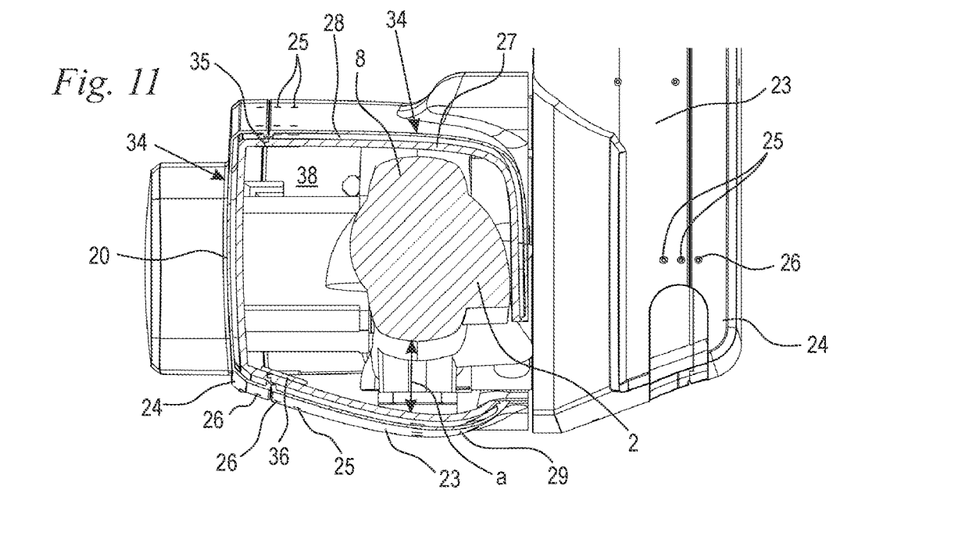
FIG. 11 is a section illustration along the line XI-XI in FIG. 10.

In the embodiment, a fastening web 36, visible in FIG. 11, is provided inside the housing unit 19, into which the fastening screws 25 and 26 are screwed. In this way, the cover 24 is secured at the base body 23. A different kind of fixation of the cover 24 on the base body 23 can be advantageous, for example, by means of fastening screws that are screwed into the base body 23 or by means of other fastening means.

In a corresponding way, the housing units 20 and 21 are constructed of a base body 23 and a cover 24, respectively. The covers 24 are arranged respectively such that components of the robot arm 25 that are to be serviced, for example, electrical drives, cable connections and the like, are easily accessible after removal of the cover 24.

Figure 10:
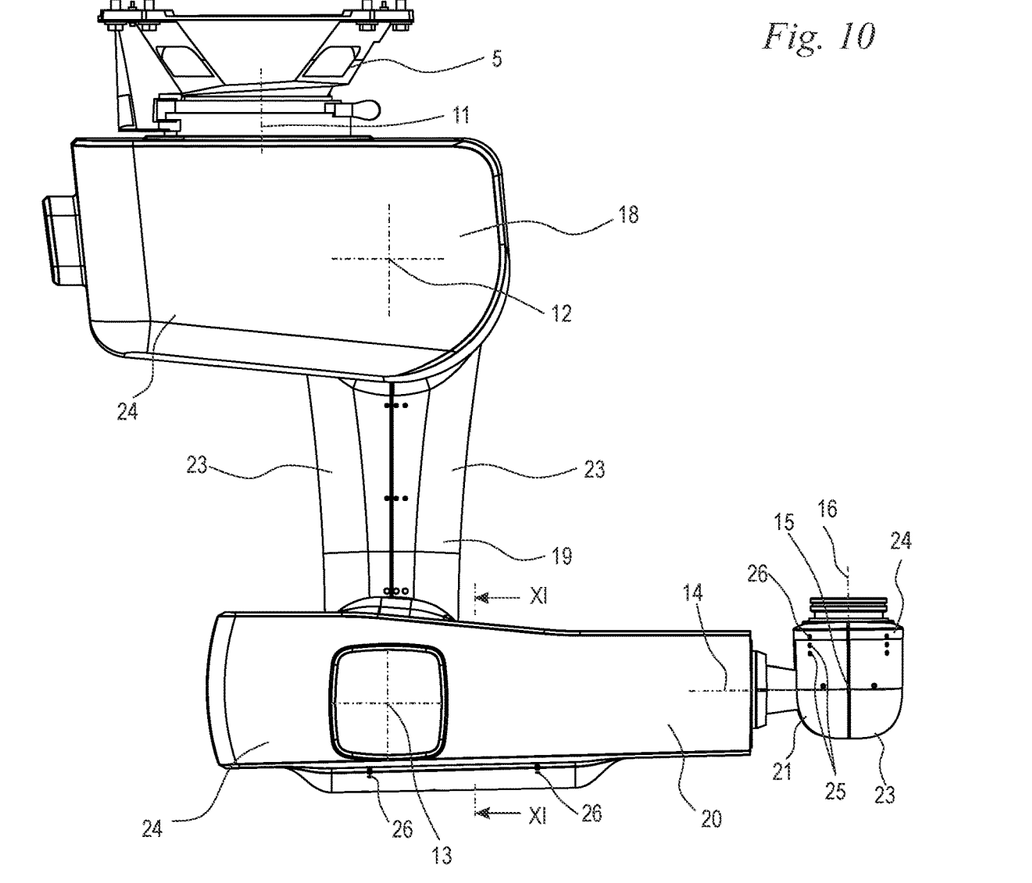
FIG. 10 is a side view in the direction of arrow X in FIG. 9.

As shown in FIG. 10, the housing unit 19 which surrounds the rocker arm 7 is of a two-shell configuration in the embodiment. The two shells of the base body 23 enclose the bearing locations at which the rocker arm 7 is pivotably supported at the carousel 6 or at the arm 8. The cover 24 of the third housing unit 19 and the cover 24 of the fourth housing unit 20 surrounding the arm 8 are attached from opposite sides to the correlated base bodies 23. The sixth housing unit 22 (FIG. 1) that surrounds the fastening flange 10 can be integrally formed at the cover 24 of the fifth housing unit 21 or can be separately embodied. The sixth housing unit 22 is advantageously not constructed of base body and cover but is completely removable with the cover 24 of the fifth housing unit 21. Advantageously, at least the housing units 18, 19, and 20 that surround the carousel 6, the rocker arm 7, and the arm 8, are constructed of base body 23 and cover 24.

As illustrated in the section illustration of FIG. 11, i.e., in the illustrated section illustration through the arm 8 of the robot arm 2, the robot arm 2 comprises about its entire circumference a distance a from the housing assembly 4. The distance a is advantageously not constant about the circumference. At every location of the circumference of the arm 8 of the robot arm 2, there is a distance a to the housing assembly 4. The distance a can be very small in this context, as illustrated, for example, in the region of the robot arm 2 to the right in the illustration. However, the housing assembly 4 also does not contact the robot arm 2 at this location.

The robot arm 2 comprises a comparatively irregular outer contour that also comprises sharp edges. In contrast thereto, the housing assembly 4 is provided with rounded edges and straight or curved contours. The housing unit 20 comprises a housing wall 34 which surrounds a housing interior 38. In the housing interior 38, the arm 8 of the robot arm 2 is arranged. As can be seen also in FIG. 11, the housing wall 34 of the housing unit 20 is of a multi-shell configuration. The additional housing units 17 to 19, 21 and 22 of the housing assembly 4 are constructed correspondingly. The housing units 17 to 22 have each an inner shell 27. In the embodiment, the inner shell 27 forms the support structure of the housing units 17 to 22. In the embodiment, the inner shells 27 are of a closed configuration with the exception of openings in the housing wall 34 which serve as through passages for connecting the sections of the robot arm 2 with each other. A rib-shaped configuration of the support structure can however be provided also. The housing wall 34 of the housing assembly 4 comprises an outer envelope 29. The outer envelope 29 in the embodiment is of a very thin configuration and advantageously elastic. Between the inner shell 27 and the outer envelope 29, a damping layer 28 is arranged whose components are not illustrated in FIG. 11.

Figure 12:
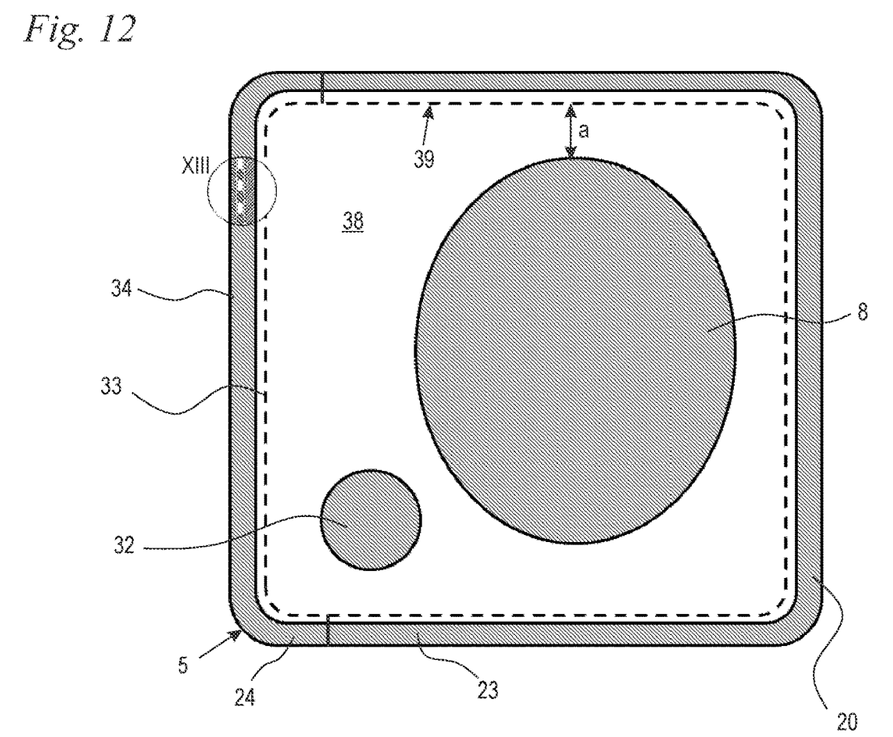
FIG. 12 shows a schematic illustration of the construction of the patient positioning device in the section plane of FIG. 11.

FIG. 12 shows schematically the arrangement of the robot arm 2 in the housing assembly 4; the arm 8 is shown in the Figure. The robot arm 2 comprises on all sides a distance a relative to the housing wall 34. As illustrated, the distance a can be differently sized at different locations of the circumference of the robot arm 2. Since there is a distance a on all sides, the robot arm 2 does not contact the housing wall 34 at any location. The housing wall 34 surrounds a housing interior 38. In the embodiment, a cable harness 32 is extending in the housing interior 38 adjacent to the arm 8. The cable harness 32 can comprise, for example, cables for power supply, for example, for supply of the electrical drives and sensors, or data lines for transmitting sensor signals. As is illustrated schematically in FIG. 12, a shielding 33 is arranged at the inner side 39 of the housing unit 20 that delimits the housing interior 38. The shielding 33 serves for shielding relative to ionizing radiation. Such a shielding can be embodied, for example, in the form of foil. Also, a shielding in the form of plates or the like can be provided. The shielding 33 is connected fixedly to the housing assembly 4. A section of the shielding 33 is fixed in this context at the base body 23 and another section of the shielding 33 at the cover 24. In a particularly advantageous configuration, the shielding 33 is glued across the surface in the base body 23 and in the cover 24.

Figure 13:
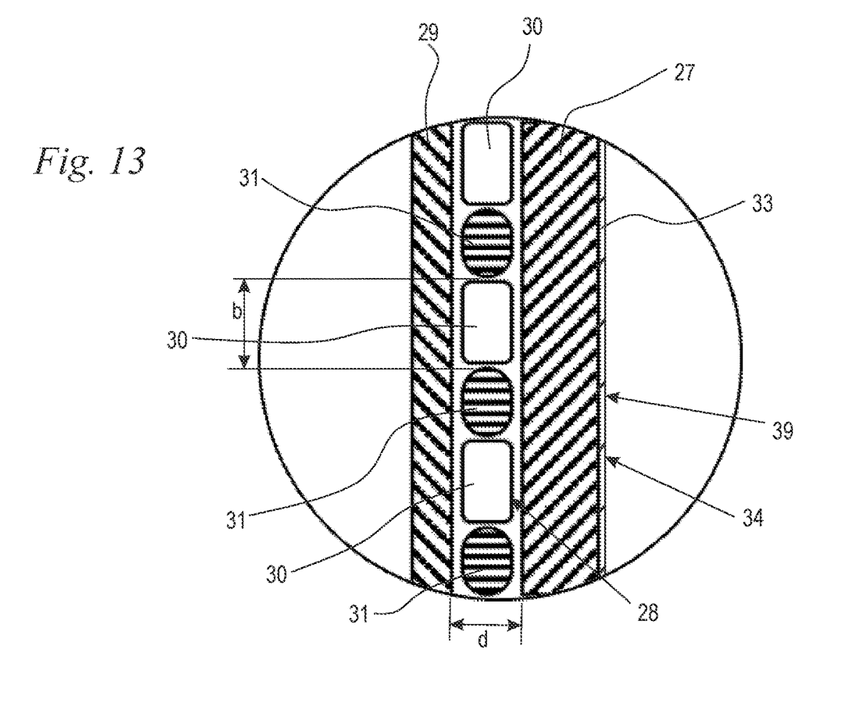
FIG. 13 shows the detail XIII of FIG. 12 in an enlarged illustration.

FIG. 13 shows the configuration of the housing wall 34 in detail. From the interior to the exterior, the housing wall 34 is constructed of shielding 33, inner shell 27, damping layer 28, and outer envelope 29. In the damping layer 28, damping material 30 is arranged. The damping material 30 can be formed, for example, by foamed material elements. Advantageously, contact sensors 31 extend between neighboring sections of the damping material 30. The contact sensors 31 can be embodied, for example, as sensing edges. The shielding 33 is arranged at an inner side 39 of the housing wall 34. The thickness d of the damping layer 28 is advantageously comparatively large. The thickness d of the damping layer 28 can amount to, for example, 0.5 cm to 15 cm. The thickness d of the damping layer 28 amounts to in particular 0.5 cm to 3 cm. The thickness d of the damping layer 28 is advantageously matched to the travel speeds of the robot arm 2 wherein large thicknesses d are advantageous for great travel speeds. The outer envelope 29 is advantageously elastic so that the damping action of the damping layer 28 is only minimally impaired by the outer envelope 29. When the outer envelope 29 contacts objects, the damping layer 28 is compressed. This dampens the forces acting on the object. Upon contact with an object, the at least one contact sensor 31 is actuated. Accordingly, the contact is recognized by the patient positioning device 1 and the robot arm 2 can be controlled accordingly, for example, stopped. Since the shielding 33 is arranged at the inner side 39 of the housing wall 34, the shielding 33 does not impair the damping characteristics of the damping layer 28. The shielding 33 is protected at the same time from mechanical effects so that damage to the shielding 33 is avoided.

In an alternative embodiment, it is provided that the damping layer 28 comprises one or a plurality of gas-filled cushions, in particular air cushions, which produce the damping action. The cushions can be covered by an outer envelope 29. Alternatively, the outwardly facing part of the cushions can form the outer envelope 29. In a preferred embodiment, the pressure within the cushions is monitored and evaluated in order to detect contact of a cushion with an object. The at least one cushion forms thus a contact sensor. A combination of gas-filled cushions and damping material may be advantageous.

In order to ensure that every contact is detected by the housing assembly 4, the distance b between neighboring contact sensors 31 advantageously amounts to less than 10 cm, in particular less than 5 cm.

As shown in FIG. 11, the base body 23 comprises a circumferential rim 35 which projects into a correspondingly shaped depression of the cover 24. In this way, the cover 24 can be positioned and pre-fixed well at the base body 23. In this way, assembly is simplified.

Figure 14:
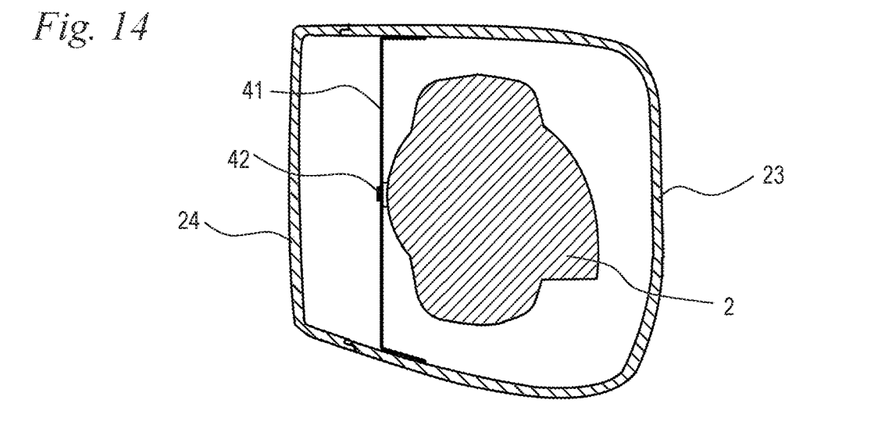
FIG. 14 shows a schematic illustration of an attachment variant of a housing unit at a robot arm.
Figure 15:
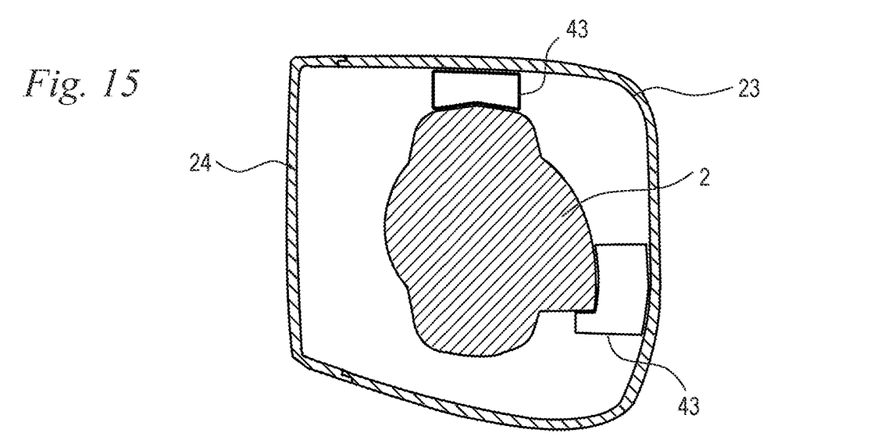
FIG. 15 shows a schematic illustration of an attachment variant of a housing unit at a robot arm.
Figure 16:
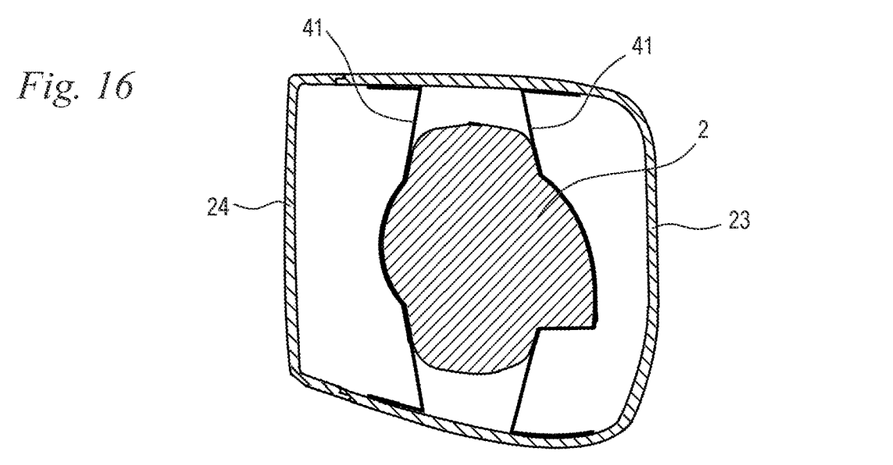
FIG. 16 shows a schematic illustration of an attachment variant of a housing unit at a robot arm.

FIGS. 14 to 16 show different variants of the fixation of the base body 23 at the robot arm 2. In the embodiment according to FIG. 14, a bracket 41 is provided which is secured with its ends at the base body 23. The bracket 41 can be screw-connected, for example, at the base body 23 or can be glued onto it. The bracket 41 is screw-connected by means of one or a plurality of fastening screws 42 at the robot arm 2. In this way, the bracket 41 fixes the base body 23 at the robot arm 2.

In the embodiment according to FIG. 15, clamping profiles 43 are fixed at the base body 23, for example, by gluing or by screws. The clamping profiles 43 surround the robot arm 2 at least partially at opposite sides. In this way, the robot arm 2 is fixed at the clamping profiles 43 with form fit. In addition, the clamping profiles 43 can be screw-connected to the robot arm 2, in particular for securing the clamping fixation.

The embodiment according to FIG. 16 shows a configuration in which at the base body 23 two brackets 41 are arranged at opposite sides of the robot arm 2. The robot arm 2 is clamped between the two brackets 41. Also, an additional fixation by one or a plurality of fastening screws can be advantageous. The bracket 41 can be fixed at the base body 23 by gluing or by means of screws. It can also be provided that the brackets 41 are held elastically at the base body 23 due to their inherent tension. Other fastening kinds for fixation of the base body 23 at the robot arm 2 can be advantageous also.

In the embodiment, the configuration of the housing unit 20 is illustrated in detail. The additional housing units 17, 18, 19, and 21 are advantageously correspondingly configured. The sixth housing unit 22 can also be configured accordingly. The configuration of the housing wall 34 is preferably the same for all housing units of the housing assembly 4. All described fixation variants for the fixation of the base body 23 at the robot arm 2 are also conceivable for all housing units 17 to 22. Other kinds of fixation may be advantageous also.

The specification incorporates by reference the entire disclosure of European priority document 20 174 076.8 having a filing date of May 12, 2020.

While specific embodiments of the invention have been shown and described in detail to illustrate the inventive principles, it will be understood that the invention may be embodied otherwise without departing from such principles.

What is claimed is:

1. A patient positioning device comprising:
   a robot arm;
   a patient receptacle held at the robot arm;
   a housing assembly configured to house the robot arm;
   the housing assembly comprising one or more housing units surrounding the robot arm at least partially;
   the one or more housing units secured to the robot arm;
   a shielding against ionizing radiation, wherein at least one part of the shielding is arranged at the housing unit.

2. The patient positioning device according to claim 1, wherein the one or more housing units comprise at least one removable cover and the at least one part of the shielding is held at the at least one removable cover and is removable together with the at least one removable cover.

3. The patient positioning device according to claim 1, wherein all parts of the shielding are fixed at the housing assembly.

4. The patient positioning device according to claim 1, wherein the shielding is arranged at an inner side of the one or more housing units.

5. The patient positioning device according to claim 1, wherein the robot arm comprises a plurality of sections, wherein the sections are movable relative to each other, and wherein each section has associated therewith one of the housing units, respectively.

6. The patient positioning device according to claim 5, wherein at least one of the housing units comprises a base body fixed at the associated section and further comprises a cover detachably secured at the base body.

7. The patient positioning device according to claim 6, wherein said at least one housing unit comprises means for positioning the cover relative to the base body.

8. The patient positioning device according to claim 7, wherein the means for positioning is a circumferential rim.

9. The patient positioning device according to claim 1, wherein the one or more housing units comprise at least partially a damping layer.

10. The patient positioning device according to claim 9, wherein the damping layer is held at a support structure of the one or more housing units.

11. The patient positioning device according to claim 10, wherein the support structure of the one or more housing units is an inner shell.

12. The patient positioning device according to claim 9, wherein the damping layer is covered by an outer envelope.

13. The patient positioning device according to claim 9, wherein the damping layer comprises an elastic damping material.

14. The patient positioning device according to claim 9, further comprising one or more contact sensors arranged in the damping layer.

15. The patient positioning device according to claim 1, wherein the robot arm comprises at least five rotation movement axes.

16. The patient positioning device according to claim 1, wherein the robot arm comprises at least six rotation movement axes.

17. The patient positioning device according to claim 1, wherein the robot arm comprises:
   a base frame,
   a carousel rotatably supported at the base frame about a first rotation movement axis;
   a rocker arm rotatably supported at the carousel about a second rotation movement axis;
   an arm rotatably supported at the rocker arm about a third rotation movement axis; and
   a hand held at the arm, wherein the hand comprises a fourth rotation movement axis, a fifth rotation movement axis, and a sixth rotation movement axis.

18. The patient positioning device according to claim 1 configured for use in a boron neutron capture therapy.

* * * * *